(12) United States Patent
Dick et al.

(10) Patent No.: US 7,926,945 B2
(45) Date of Patent: Apr. 19, 2011

(54) DEVICE AND METHOD FOR MONITORING, DOCUMENTING AND/OR DIAGNOSING THE FUNDUS

(75) Inventors: Manfred Dick, Gefell (DE); Thomas Mohr, Jena (DE); Daniel Bublitz, Jena (DE); Peter Westphal, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 405 days.

(21) Appl. No.: 11/988,965

(22) PCT Filed: Jul. 19, 2006

(86) PCT No.: PCT/EP2006/007089
§ 371 (c)(1),
(2), (4) Date: Jan. 17, 2008

(87) PCT Pub. No.: WO2007/009761
PCT Pub. Date: Jan. 25, 2007

(65) Prior Publication Data
US 2009/0153798 A1    Jun. 18, 2009

(30) Foreign Application Priority Data

Jul. 22, 2005    (DE) .................... 10 2005 034 332

(51) Int. Cl.
*A61B 3/14* (2006.01)
*A61B 3/00* (2006.01)
(52) U.S. Cl. ............ 351/206; 351/205; 351/246
(58) Field of Classification Search ............ 351/200, 351/205, 206, 246
See application file for complete search history.

(56) References Cited

U.S. PATENT DOCUMENTS

| | | | |
|---|---|---|---|
| 3,760,174 | A | 9/1973 | Boenning et al. |
| 5,836,872 | A | 11/1998 | Kenet et al. |
| 5,926,283 | A | 7/1999 | Hopkins |
| 5,982,497 | A | 11/1999 | Hopkins |
| 5,983,120 | A | 11/1999 | Groner et al. |
| 5,997,141 | A | 12/1999 | Heacock |

(Continued)

FOREIGN PATENT DOCUMENTS

DE    25 12 427    1/1976

(Continued)

*Primary Examiner* — Joseph Martinez
*Assistant Examiner* — James R Greece
(74) *Attorney, Agent, or Firm* — Frommer Lawrence & Haug LLP (57) ABSTRACT

The present invention is directed to a device and a method for the observation, documentation and/or diagnosis of the fundus in which the diagnosis is carried out by evaluating the documented images of the fundus. The device according to the invention comprises an ophthalmological examination device, a multi-spectral sequential illumination module, an image recording module, a control and safety module, and an evaluating unit. The illumination module which is connected to the ophthalmologic examination device has at least two individual light sources and which can be regulated individually with respect to intensity and duration and which emit monochromatic light of different wavelengths. The light coming from the illumination module is imaged on the image recording module from the ophthalmologic examination device by the eye being examined. The control and safety module controls the chronological sequence, duration and intensity of the individual light sources and monitors the light stress. An evaluating unit evaluates the recordings of the fundus transmitted by the image recording module. The inventive solution serves to record monochromatic images of the retina, for example, red, green, blue, or also infrared, and to record fluorescence images.

66 Claims, 4 Drawing Sheets

U.S. PATENT DOCUMENTS

| | | | |
|---|---|---|---|
| 6,000,799 A | 12/1999 | Van de Velde | |
| 6,005,717 A * | 12/1999 | Neuberger et al. | 359/619 |
| 6,099,127 A * | 8/2000 | Manivannan et al. | 351/221 |
| 6,276,798 B1 | 8/2001 | Gil et al. | |
| 6,373,568 B1 | 4/2002 | Miller et al. | |
| 6,454,410 B1 | 9/2002 | Berger et al. | |
| 6,549,801 B1 | 4/2003 | Chen et al. | |
| 6,714,672 B1 | 3/2004 | Berestov et al. | |
| 2004/0064057 A1 | 4/2004 | Siegel | |
| 2004/0075812 A1 | 4/2004 | Kardon et al. | |
| 2004/0105074 A1 | 6/2004 | Soliz et al. | |
| 2005/0267343 A1 | 12/2005 | Woods et al. | |
| 2006/0100528 A1 | 5/2006 | Chan et al. | |

FOREIGN PATENT DOCUMENTS

| | | |
|---|---|---|
| DE | 30 41 178 | 5/1981 |
| DE | 196 26 433 | 1/1998 |
| EP | 0 631 757 | 1/1995 |
| EP | 1 084 674 | 3/2001 |
| EP | 1 084 675 | 3/2001 |
| EP | 1 114 608 | 3/2003 |
| EP | 0 801 534 | 12/2003 |
| EP | 1 611 840 | 1/2006 |
| JP | 10-314118 | 12/1998 |
| WO | 92/02173 | 2/1992 |
| WO | 96/09792 | 4/1996 |
| WO | 97/05538 | 2/1997 |
| WO | 02/080759 | 10/2002 |

* cited by examiner

DEVICE AND METHOD FOR MONITORING, DOCUMENTING AND/OR DIAGNOSING THE FUNDUS

CROSS-REFERENCE TO RELATED APPLICATIONS

This is a national phase application of International Application No. PCT/EP2006/007089, filed Jul. 19, 2006 which claims priority of German Application No. 10 2005 034 332.5, filed Jul. 22, 2005, the complete disclosures of which are hereby incorporated by reference.

a) FIELD OF THE INVENTION

The present invention is directed to a device and a method for the observation, documentation and/or diagnosis of the fundus in which the diagnosis is carried out by evaluating the documented images of the fundus, in particular the ophthalmological diagnostic features of the retina contained therein such as, for example, the blood flow velocity in the vessels of the fundus.

b) DESCRIPTION OF THE RELATED ART

Besides the classic ophthalmologic instruments for examining the fundus, the known prior art also discloses laser scanning systems or multi-spectral sensor systems with optical beam separation in the observation beam path. The systems usually have means for recording and processing digital images.

In classic fundus cameras, there are disadvantages in using mechanically swivelable filters for recording monochromatic images, e.g., red, green, blue (RGB). Although the retina is illuminated over a broad band by white light, e.g., halogen lamps or xenon flash lamps, for color recordings, the electronic evaluation is carried out only in a very narrow-band range. For this purpose, color masks are placed on the electronic image receiving sensor of the documentation camera. Further, in classic fundus cameras affording optical observation, the retina is illuminated continuously so that the light stress on the eye being examined is especially high. The narrow-band excitation in the range of 20 nm to 40 nm which is required for diagnostics can only be realized through costly filters which must also be swiveled into and out of the beam path in the millisecond range. An opthalmoscope for observing and photographing the fundus which is typical of this group is described in DE 25 12 427 A1.

An ophthalmologic device with an optical irradiation system for irradiating a patient's eye is described in EP 1 114 608 B1. The optical irradiation system comprises a plurality of LEDs and an optical system for combining the optical light beams of the LEDs. Further, the device has an arrangement for controlling the amount of light in order to change a ratio of the amount of light emitted by the LEDs in cooperation with the insertion and/or removal of the protective filter that prevents the treatment laser beam from entering the eye of the operator.

U.S. Pat. No. 5,997,141 A likewise discloses an ophthalmologic instrument with an irradiation system for irradiating a patient's eye having a plurality of LEDs and a light quantity control device for controlling the amount of light emitted by each of the LEDs.

A programmable light source is described in U.S. Pat. No. 3,760,174 A. In this case, also, individually controlled LEDs can ensure that a determined irradiation spectrum is provided. As a rule, the provided irradiation spectrum is a mixed light signal.

When laser scanning systems are used for examining the fundus, simultaneous observation is impossible. Further, the laser sources needed for confocal imaging are relatively expensive. Also, the laser beam must be deflected by correspondingly elaborate arrangements in order to carry out a scan over the surface of the retina.

In contrast, arrangements for deflection can be dispensed with when using a two-dimensional multi-spectral spectrometer. With the arrangements described in U.S. Pat. Nos. 5,926,283 A1 and 5,982,497 A1, spectrally separated, two-dimensional images of the object to be examined can be determined simultaneously in real time.

The optical beam separation in the observation beam path which is provided in multi-spectral systems, e.g., Quad-View, can be realized optically only with much effort, which is further exacerbated by problems with reflected and scattered light. Further, only small viewing angles of about 20° can be achieved. The light stress on the eye under examination caused by broadband excitation with white light is also very great in this case, and there are problems with reflections and scattered light in the observation beam path as well.

According to the prior art, fundus photographs having a resolution of 5 to 8 megapixels are taken with color cameras. In order to generate the very high light powers needed for these unresponsive cameras, combinations of halogen lamps (observation) and flash lights (documentation) are used. These systems have the drawback that very high light powers must be used to produce fundus images with the necessary dynamics. Also, the use of flash lamps necessitates very complicated control electronics and increased maintenance for replacing burnt out flash lamps. Further, the high resolution of 5 to 8 megapixels is not needed for many applications to be implemented with the fundus camera. On the contrary, sensitive sensors are often needed to register the very weak light signals. This is compounded by the fact that the light dose required for recording must be further reduced in order to minimize the light stress on the eye under examination.

The blood flow in the retina and fundus has great physiological importance for the functionality of the eye and may possibly also be an indicator of other health conditions in humans. The microcirculation of the red blood cells (erythrocytes) is considered an important physiological parameter at least in sepsis research and heart surgery. In combination with information about the oxygen saturation in the same area of the body, its informational value can be even further substantially increased.

There are already optical methods (DE 30 14 178 C2) by which the entire blood supply to the fundus can be measured using the Doppler effect. However, these measurement methods have no spatial resolution and are therefore of limited usefulness. In particular, no information can be gathered in this way about the microcirculation of the blood.

Determination of the blood flow velocity in the vessels of the fundus has been investigated, for example, by Doppler techniques (DE 30 41 178 C2). For this purpose, the blood flow velocity component perpendicular to the fundus plane is measured at the point where the vessels enter the fundus by determining the Doppler frequency shift of a laser wave reflected in the blood. The problem with this method is that only perpendicular velocity components in relation to the plane of the fundus can be measured. This is a problem inasmuch as the vessels in the fundus extend tangentially and therefore perpendicular velocity components occur only at the point where the vessels enter the fundus. For this reason, a laser wave is radiated into the eye from two different directions so that the tangential component of the blood flow velocity can also be determined from the difference in frequency between the two light bundles. Further, the method of spatially resolved measurement of the Doppler frequency shift requires substantial technical resources.

U.S. Pat. No. 5,983,120 A1 describes a solution for reflected image analysis for performing noninvasive, in vivo analysis of vascular systems. A reflected image is normalized with respect to the background and segmented to analyze an image section of interest. For example, the concentration of hemoglobin, i.e., the number of red blood cells per unit volume of blood, can be determined by the proposed solution through tissue of a thickness up to 0.5 mm. However, the solution is not readily usable for measuring the blood flow at the retina or at the fundus.

A method for visualizing a first and a second layer of blood vessels is described in EP 1 084 674 B1. While the choriocapillaries in particular can be made visible in relation to the other blood vessels in the choroid with the method based on intravenous injection of fluorescent dyes, a spatially resolved blood flow measurement is impossible.

The solution described in EP 0 801 534 B1 for optically displaying the blood circulation and abnormal vessel structures in the choroid of the eye is also based on intravenous injection of a fluorescent dye. The dye fills the vasculature of an eye, emits fluorescence through excitation, and accordingly images the vasculature on an angiographic image.

WO 97/05538 A1 describes an optical method for blood flow measurement. The essential component in this solution is a controllable, spatially resolved modulator having a quantity of areas which are individually controllable with respect to transmission. A radiation-sensitive area of a spatially resolving detector is allocated to each of these areas of the modulator.

U.S. Pat. No. 6,549,801 B1 claims an OCT-like construction. This means that the overlapping and interference of light of the primary arm with reference light is the essential structural feature.

In the method described in JP10314118 A1, the blood flow velocity is measured by registering a time-resolved signal with the point detector. Fourier transformation of this signal yields the cutoff frequency as a measure of the flow velocity. However, to do this, the signal of the detector must be registered with a high time resolution. This time resolution can be achieved only with much difficulty with a spatially resolved detector such as a CCD camera. In the method presented, a spatially resolved detector (for simple two-dimensional measurement of the relative flow velocity) is combined with a fast point sensor (for point-oriented measurement of the absolute flow velocity). Therefore, the method is extremely demanding and costly in technical respects.

There is a prior art method called speckle correlation technique which makes possible a very simple and accurate measurement of movements of scattering surfaces.

When a scattering surface is illuminated by a laser or a light source with high spatial and temporal coherence, the light backscattered from the surface can interfere in space and produce the typical grainy structures (speckle) known from laser techniques. This speckle is seen, for example, when a visible laser is expanded and directed to a scattering surface (sheet of paper, wall). A distinction is made between subjective speckle and objective speckle. Subjective speckle occurs when the scattering surface is imaged on the camera sensor by optics. Subjective speckle is exactly equal to the optical resolution of the imaging system. The scatter pattern that is registered moves along with the scattering surface through displacements, and it is therefore possible to determine the displacement.

Objective speckle occurs when the camera sensor is placed in the light backscattered from the sample without optics. Objective speckle reacts to tilting of the sample surface. The size of the objective speckle is calculated from the wavelength of the radiation, the diameter of the illuminated sample surface, and the distance between the sample surface and the camera sensor.

In the following, the term "fundus" serves as an umbrella term for the following anatomical structures of the eye:
  retina
  optic disk (papilla)
  vessels (arteria and vena centralis retinae)
  yellow spot (macula lutea)
  retinal periphery and ora serrata (junction between retina and ciliary body).

The blood flow defines the supply of nutrient and active materials and transport capacity of metabolic products to a vascular region. However, interchange ratios determine whether or not the supply reaches the tissue area to be supplied in the required amount and time.

Vessel diameters are, on the one hand, controlling elements of local regulatory mechanisms, but on the other hand are also target sites for age-related, pathological, and therapeutic activity. From this can be derived a highly innovative potential for vessel analysis for risk analysis, early detection, prognostics, diagnostics, and therapy for diseases of the eye and possibly also for other medical disciplines.

It must be taken as granted that the in-vivo behavior in time and space of the diameter of a vessel segment reflects the combined effect of various competing, redundant and complementary regulating chains which act with different dynamics and in different vessel areas at differing strengths.

OBJECT AND SUMMARY OF THE INVENTION

It is the primary object of the present invention to provide a solution for recording sensitive, highly resolved images of the retina from which information about possible diseases can be diagnosed by electronic post-processing and evaluation. The solution, which is preferably non-mydriatic, affords viewing angles of up to 45° and minimizes the light stress on the eye to be examined.

Based on images of the retina, it should be possible to determine the blood flow in the retina and in the fundus for purposes of early diagnosis of important information about functional disorders and possible diseases.

According to the invention, the above-stated object is met in a device for the documentation and/or diagnosis of the fundus, a multi-spectral sequential illumination module, a control and safety module, and an evaluating unit. An illumination module is connected to the ophthalmologic examination device having at least two individual light sources which can be regulated individually with respect to intensity and duration and which emit monochromatic light of different wavelengths. The light coming from the illumination module is imaged on the image recording module from the ophthalmologic examination device by the eye being examined. The image recording module which is likewise connected to the ophthalmologic examination device is tuned to the wavelengths of the light emitted from the illumination module and synchronized with the illumination period. The control and safety module controls the chronological sequence, duration and intensity of the individual light sources of the illumination module and monitors the light stress. The evaluating unit regulates the control and safety module and assesses, corrects, improves, combines, superimposes in a positionally exact manner, and evaluates the recordings of the fundus transmitted by the image recording module.

Also in accordance with the invention, the above stated object is met by a method for the observation, documentation and/or diagnosis of the fundus comprising the steps of imaging the light of a multi-spectral sequential illumination module on an image recording module by the eye by an ophthalmologic examination device and connecting the illumination module to the ophthalmologic examination device. The illumination module comprises at least two individual light sources which can be regulated individually with respect to intensity and duration emit monochromatic light of different wavelengths which is imaged on the image recording module by the ophthalmologic examination device by the eye being examined. The method also includes the steps of connecting the image recording module to the ophthalmologic examination device and tuning it to the wavelengths of the light emitted by the illumination module and synchronizing it with illumination periods of the illumination module, providing that a control and safety module controls the chronological sequence, duration and intensity of the individual light sources of the illumination module and monitoring the light stress on the eye being examined, and providing that the evaluating unit regulates the control and safety module and assesses, corrects, improves, combines, superimposes in a positionally exact manner and evaluates the recordings of the fundus transmitted by the image recording module.

The solution according to the invention is used for taking monochromatic pictures of the retina, for example, red, green, blue, or infrared, and for making fluorescence images. In particular, fluorescence images can also be made in the infrared spectral region using the dye known as indocyanine green (ICG).

The invention will be described in the following with reference to an embodiment example.

BACKGROUND OF THE INVENTION

DESCRIPTION OF THE PREFERRED EMBODIMENTS

The device according to the invention for observing, documenting and/or diagnosing the fundus comprises an ophthalmological examination device, a multi-spectral sequential illumination module, an image recording module, a control and safety module, and an evaluating unit.

Figure 1:
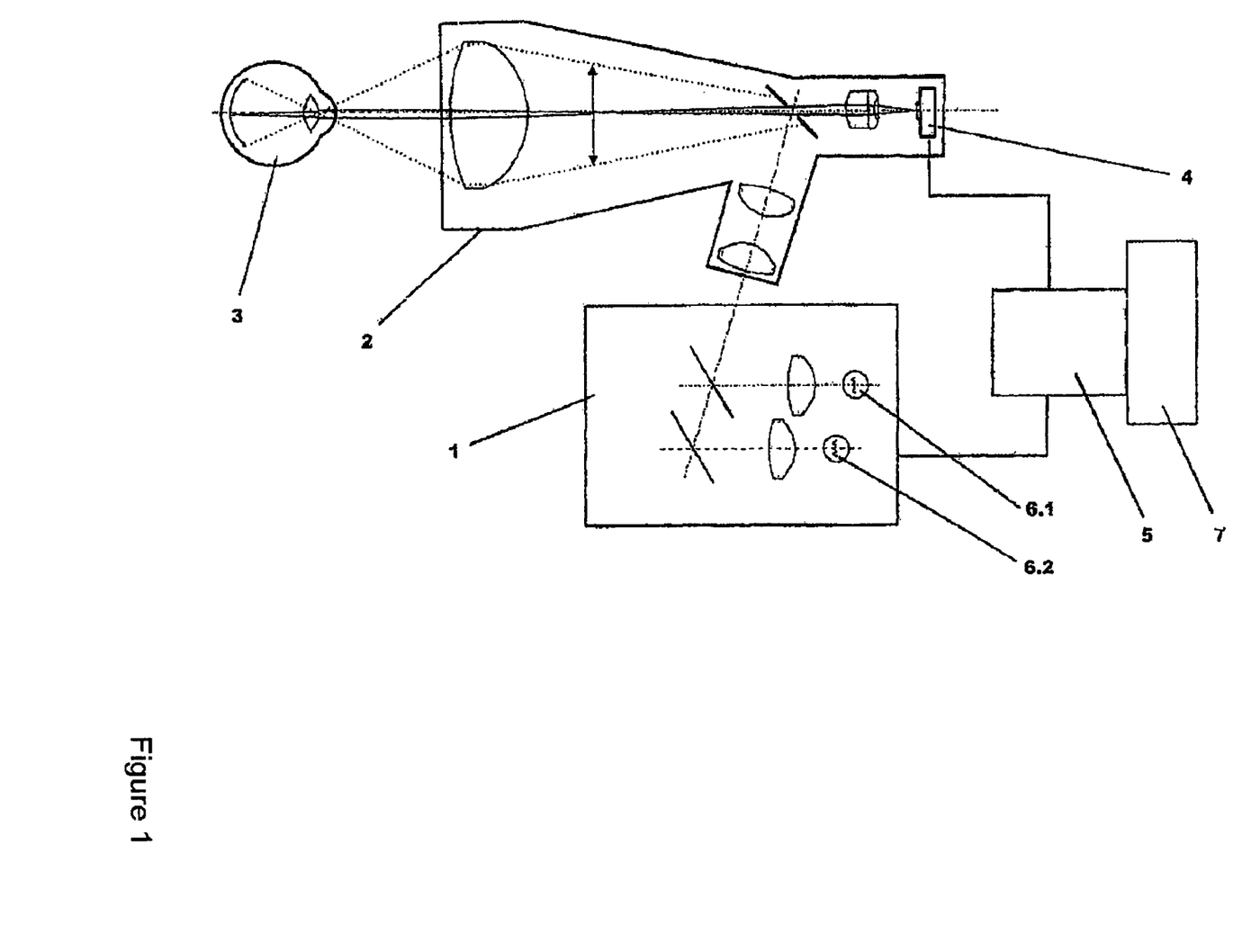
FIG. 1 is a schematic illustration of a fundus camera for carrying out the method according to the invention.

FIG. 1 shows a schematic view of a fundus camera for carrying out the method according to the invention. The light emitted by the multi-spectral sequential illumination module 1 is projected on the eye 3 by the fundus camera 2. The light reflected by the eye 3 is imaged onto the image recording module 4 by the fundus camera 2. A control and safety module 5 controls the chronological sequence, duration and intensity of the individual light sources 6.1 and 6.2 of the illumination module 1 and monitors the light stress on the eye 3. The evaluating unit 7, also provided, regulates the control and safety module 5 and processes the images delivered by the image recording module 4 with respect to contrast, image sharpness, chromatic errors, pixel errors, border falloff, distortion, local alignment, and the like and also evaluates them. In a particular constructional variant, a light guide or light-guide bundle is arranged between the illumination module 1 and the fundus camera 2 for transmitting the light of the individual light sources 6.1 and 6.2 which can be coupled by light-mixing rods and/or microlens arrays. The light-mixing rods and/or microlens arrays serve to homogenize the illumination radiation.

The illumination module which is connected to the ophthalmologic examination device has at least two individual light sources which can be regulated individually with respect to intensity, time and duration and which emit monochromatic light of different wavelengths, preferably in the range from 350 to 900 nm.

The light coming from the illumination module is imaged on the image recording module by the ophthalmologic examination device by means of the eye being examined, and the image recording module which is likewise connected to the ophthalmologic examination device is tuned to the wavelengths of the light emitted from the illumination module and synchronized with its illumination periods.

The control and safety module controls the chronological sequence, duration and intensity of the individual light sources of the illumination module and monitors the light stress. The evaluating unit regulates the control and safety module and assesses, corrects, improves and combines the recordings of the fundus transmitted by the image recording module for evaluation.

In an advantageous construction, individual light sources whose turn-on and turn-off delay is under 1 ms are used for the illumination module. This means that every beam can be switched on from 0 to 100% intensity within a time period of less than 1 ms and can also be turned off again from 100% to 0 within this time.

When using more than two individual light sources, not only two-dimensional arrangements but also three-dimensional arrangements are conceivable. The beam bundles generated by the individual light sources are coupled with one another by mirrors and/or gratings, preferably having a dichroic characteristic, in such a way that they coincide in aperture and aperture angle at the point of connection to the ophthalmologic examination device and generate an image with the most constant possible angular spectrum at that point.

The beam bundles generated by the individual light sources having the narrowest possible band coincide with respect to aperture and aperture angle at the point of connection to the ophthalmologic examination device and generate an image with the most constant possible angular spectrum. The invention is based on the principle of geometrically separating the illumination beam path and observation beam path. In addition to the annular pupil illumination used in most fundus cameras, other geometric separations of the illumination beam path and observation beam path are also possible in principle.

Another construction could generate a circular imaging for the illumination beam path. The observation beam path is then likewise circular and the two beam paths extend side by side. The optical output of the individual light sources should be at least 1 milliwatt at the interface.

In particular, LEDs, with or without filters arranged in front of them, or diode lasers can be used as individual light sources. The best possible coverage of the color space should be achieved. Available LEDs with the highest possible output are relied upon in practice. In particular, the individual light sources are selected in such a way that sensitive, high-resolution images of the retina are recorded and information about possible diseases can be diagnosed by electronic post-processing and evaluation.

When using lasers for illuminating the fundus at very high intensities, the coherence of the laser radiation is substantially reduced by means of a suitable device in an advantageous construction to achieve a homogeneous, two-dimensional illumination. In assessing the hazard posed by optical radiation, coherent radiation is judged to be more dangerous than incoherent radiation; accordingly, incoherent radiation is preferably always used for high-energy, extensive illumination of the fundus. A device for reducing the coherence of laser radiation can be constructed, for example, by means of a scatter filter or a rotating mirror.

However, the coherent characteristics of the laser light are made use of to measure the blood flow velocity by the speckle correlation technique. In this case, the spatial coherence must not be impaired by taking additional steps, which can be achieved in this particular construction, for example, by stopping the rotating mirror.

A radiation source based on a gas discharge can also be used for high-energy, two-dimensional pulsed illumination of the fundus. A radiation source of this type emits inhomogeneous radiation. However, it is disadvantageous that the gas discharge can only be operated for a relatively short time (in the range of a few milliseconds) and a subsequent cooling phase (in the range of 50 to 100 ms) is required.

For example, an LED emitting infrared light can be used as a monitor LED for adjusting the image. LEDs emitting blue light are used for fluorescence recordings. When two LEDs which emit blue (488 nm) and green (532 or 550 nm) light are used, the macular pigment density, i.e., the xanthophyll concentration, can be determined. In a special method of fluorescence angiography, the vascular system of the choroid can be examined by using the dye ICG which is excited in the range of 730 to 780 nm.

LEDs with the colors red, green and blue (RGB) are required, for example, for determining a resulting color image. In the so-called quadview analog, four LEDs with special yellow and green wavelengths are used. This makes it possible, for example, to detect a scaled difference between oxygen-saturated blood and unsaturated blood.

When using LEDs with specially adapted emission wavelengths, a comprehensive diagnosis is possible through electronic post-processing and evaluation of the monochromatic recordings of the retina. The quantity of LEDs used is unlimited.

In particular, the control and safety module controls only those individual light sources with appropriate duration and intensity that are required for the specific examination. The control and safety module synchronizes the image recording module with the illumination module so that an image, preferably also a plurality of associated images, is realized with optimal contrast, i.e., with the highest possible signal-to-noise ratio, at every wavelength. The fill factor of the electronic sensors which is usually in the range of 40 to 60% is appreciably increased to $\geq 90\%$ by the microlens array. A sensitive monochromatic digital camera with an average resolution of about 1 megapixel is used as image recording module, for example. The image converter chip of the camera can contain a microlens array to achieve the highest possible surface area fill density.

The evaluating unit processes the images delivered by the image recording module with respect to contrast, image sharpness, color errors, pixel errors, border falloff, distortion, local alignment error, and the like. But at least one image, preferably a plurality of images, is recorded in different colored illumination states with an exposure time of several milliseconds.

In particular, the individual images supplied by the image recording module are evaluated by the evaluating unit with respect to their quality, existing image errors such as image sharpness, pixel errors, border falloff, and distortion are corrected, the quality of the recordings is improved with respect to contrast and sharpness, and relevant information for functional diagnostics is extracted.

For example, a color image of the fundus can be determined by the evaluating unit from the various monochromatic images supplied by the image recording module. But it is also possible for the evaluating unit to determine an image having a resolution in the subpixel range from the individual images supplied by the image recording module. In both cases, an existing local alignment error is corrected so that the individual images are superimposed exactly.

In another advantageous embodiment of the solution according to the invention, the ophthalmologic examination device is a fundus camera which preferably operates on the non-mydriatic principle. The imaging should preferably be carried out in infinity and focused on the retina by the eye lens.

In another embodiment, the ophthalmologic examination device has a device for monitoring and compensating for eye movement. In this way, eye movement can be detected and can be tracked by the sensor of the image recording module 4 by means of an actuator, for example, a piezo drive.

In another advantageous construction, a first polarization filter is associated with the multi-spectral sequential illumination module 1 and a second polarization filter is associated with the image recording module 4 for measuring blood flow. These polarization filters which are preferably constructed as linear or circular polarizers are located in the collimated illumination beam path and detection beam path, respectively. The two polarization filters are adjusted with respect to one another in such a way that the light directly reflected by the eye is suppressed to a maximum extent so that only the light that is scattered multiple times and, therefore, depolarized reaches the image recording module 4.

To measure blood flow, the fundus is illuminated by the illumination module 1 with polarized light, preferably linearly or circularly polarized light, and only the light that is reflected by the fundus, scattered repeatedly, and depolarized is recorded by the image recording module 4 in the form of at least two immediately successive recordings and forwarded to the evaluating unit 7 for a spatially resolved correlation analysis. The brightness contrast on the image recording module 4 then results from, among others, the penetration depth of the scattered illumination light because more deeply penetrating light is scattered more often, and is therefore more depolarized, on the return path to the image recording module 4. Typically, a photon must be scattered more than ten times to be depolarized in the statistical mean.

To compensate for the birefringence of the cornea, eye lens, retina and/or optical components of the ophthalmologic examination device, at least one birefringence compensator is provided and is preferably formed as a variable birefringence compensator with a position-dependent compensation characteristic.

This can be, for example, a Babinet compensator or a Soleil compensator which are known from the prior art. Both compensators can compensate for different strengths of the phase shift between s-light and p-light and different positions of the polarization ellipse.

Figure 4:
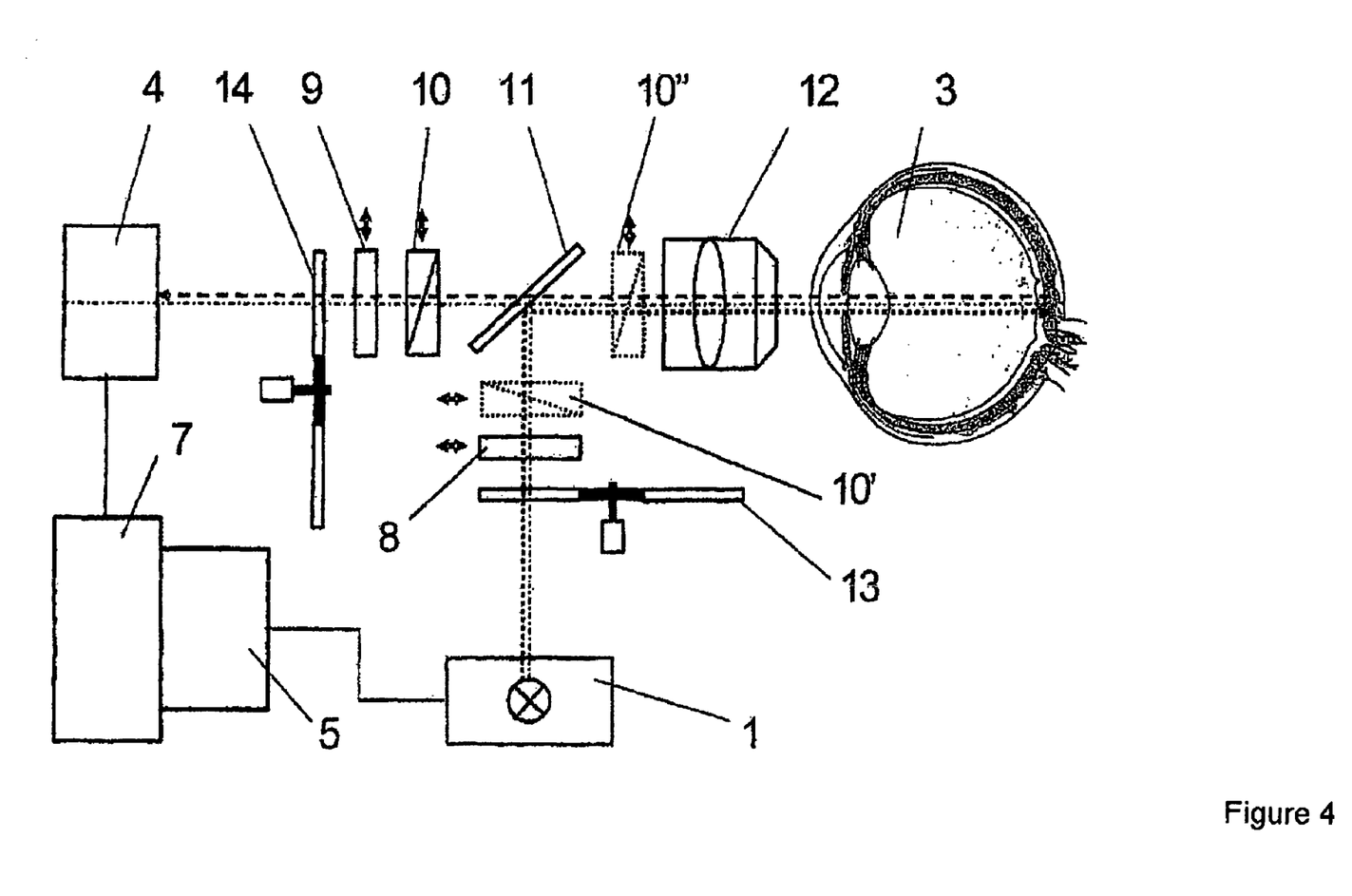
FIG. 4 shows the arrangement, according to the invention, for measuring the blood flow at the fundus.

An arrangement according to the invention for measuring blood flow at the fundus is shown in FIG. 4. A first polarization filter 8 is arranged in front of the multi-spectral sequential illumination module 1, and a second polarization filter 9 is arranged in front of the image recording module 4.

The birefringence compensator 10 provided for compensation is preferably arranged in front of the polarization filter 9 in the detection beam path.

In principle, however, the birefringence compensator 10' can also be arranged in the illumination beam path for precompensation of birefringence, or between a beamsplitter 11 and objective 12 (designated as 10"). It is even possible in principle to use a plurality of birefringence compensators 10, 10' and 10".

Since the birefringence of the cornea is relatively constant in the central area (near the optic axis) but can vary spatially farther outside of the latter, it is advantageous to use birefringence compensators 10 which have a spatially variable compensation characteristic.

In each case, all of the elements that influence polarization such as polarization filters 8, 9 and birefringence compensators 10 are adjusted relative to one another in such a way that the contents of the blood vessels appear with maximum contrast on the image-generating sensor.

A lateral resolution from 1 to 7 µm is used for image generation in order to resolve, at least roughly, the red blood cells (erythrocytes) which in humans have a diameter of about 7.5 µm. However, resolutions from 7 to 20 µm could also be sufficient for obtaining an adequate spatial contrast from the interior of the blood vessel.

In order to measure the blood flow and blood flow velocity, at least two immediately successive recordings of the fundus are subjected to a spatially resolved correlation analysis. In so doing, it is determined how far the brightness profiles along individual blood vessels have shifted in the time interval between recordings. These brightness profiles are caused by the random spatial distribution of the erythrocytes which persists for a certain time in every blood vessel in spite of the blood flow.

In another advantageous construction for measuring the oxygen content of blood, at least one color filter is arranged in front of the multi-spectral sequential illumination module 1 or in front of the image recording module 4, and recordings of the fundus are made by the image recording module 4 with and without a color filter and are sent to the evaluating unit 7. Color filters may be dispensed with when light of the appropriate wavelength can be made available by the multi-spectral sequential illumination module 1.

The measurement of the oxygen content of blood is always a spatially resolved measurement of the oxygen saturation, that is, a charting of the oxygen saturation over the fundus, and a distinction must be made between the oxygen saturation in the vessels and the oxygen saturation in the capillary region.

In order to measure the oxygen saturation, at least two recordings must be made with two different illumination spectra. The reflectivity of the fundus which is dependent (locally dependent) on the illumination spectra is determined by the absorption spectrum of oxygenated and deoxygenated hemoglobin among others. In addition, it is possible that the spectrum that is reflected back depends at the same time on other parameters that are unknown at the time of measurement, e.g., vessel thickness or hematocrit (proportion by volume of red blood cells in the blood). Through illumination and detection in suitable wavelength regions, it is possible to extract (also in a spatially resolved manner) all of these parameters at once from the measured data. In the event that there are a plurality of (more than two) parameters (quantity: n) that are unknown at the time of measurement, at least n measurements must be carried out with different pairs of illumination spectra suited to the specific problem.

In order to measure the oxygen content of the blood, two recordings of the fundus must be made by the image recording module 4 in two different wavelengths and sent to the evaluating unit 7. For this purpose, it is necessary to use at least one, but preferably two, color filters which are arranged alternately in front of the illumination module 1 or in front of the image recording module 4 and introduced into the beam path for a recording. Two filter wheels are provided for changing the illumination wavelength and detection wavelength.

Recordings of the fundus can be made in two different wavelengths by changing the wavelength of the illumination light or by inserting color filters in front of the image recording module 4 with broadband illumination.

FIG. 4 shows that the color filters can advantageously be arranged on a filter wheel. In addition, fluorescence recordings of the fundus can be made with this arrangement through a suitable combination of color filters in filter wheel 13 and filter wheel 14.

To make conventional fundus camera recordings, all polarization filters and compensators are designed in such a way that they can be swiveled out of the beam paths.

To this end, the filter changers have positions without filters (when using color cameras) or positions with red, green and blue filters (when using black-and-white cameras). The use of color filters can be dispensed with here as well when light of appropriate wavelengths can be made available by the multi-spectral sequential illumination module 1.

It is advantageous when the required recordings of the fundus are made at wavelengths of approximately 650 nm and approximately 810 nm. While there is no difference between the spectra of oxygenated and deoxygenated hemoglobin at 810 nm, these spectra differ very sharply at 650 nm so that the oxygen saturation can be determined directly. At a wavelength of 650 nm, the red blood pigment (hemoglobin) has a particularly high absorption so that the blood vessel and its content appear darker than the surrounding tissue. In this way, the locally differing absorption of the fundus can be compensated at the same time. For this purpose, either one filter is used which is transparent for one of the wavelengths while the other wavelength is covered by the illumination module 1, or two filters are used whose pass-band corresponds to these two wavelengths.

In this connection, it must be taken into account that the absorption of hemoglobin below approximately 610 nm is particularly high and the absorption of oxygenated hemoglobin has a minimum in the region of 690 nm. To achieve the best possible contrast in front of the fundus, arteries (highly oxygenated hemoglobin) must always be imaged in the range of less than 610 nm and veins (less highly oxygenated hemoglobin) must be imaged at less than approximately 800 nm. To achieve a good contrast for both types of vessel with small diameters, a wavelength of less than approximately 600 nm must be provided. In this wavelength region, the blood vessels generally appear darker than the surrounding tissue.

Another important factor influencing contrast is the locally differing absorption of the fundus. To maximize this effect, illumination wavelengths in which the red blood pigment (hemoglobin) has a high absorption (approximately 500 to 600 nm) are preferably used. Accordingly, the blood vessels and their contents appear darker than the surrounding tissue.

Figure 5:
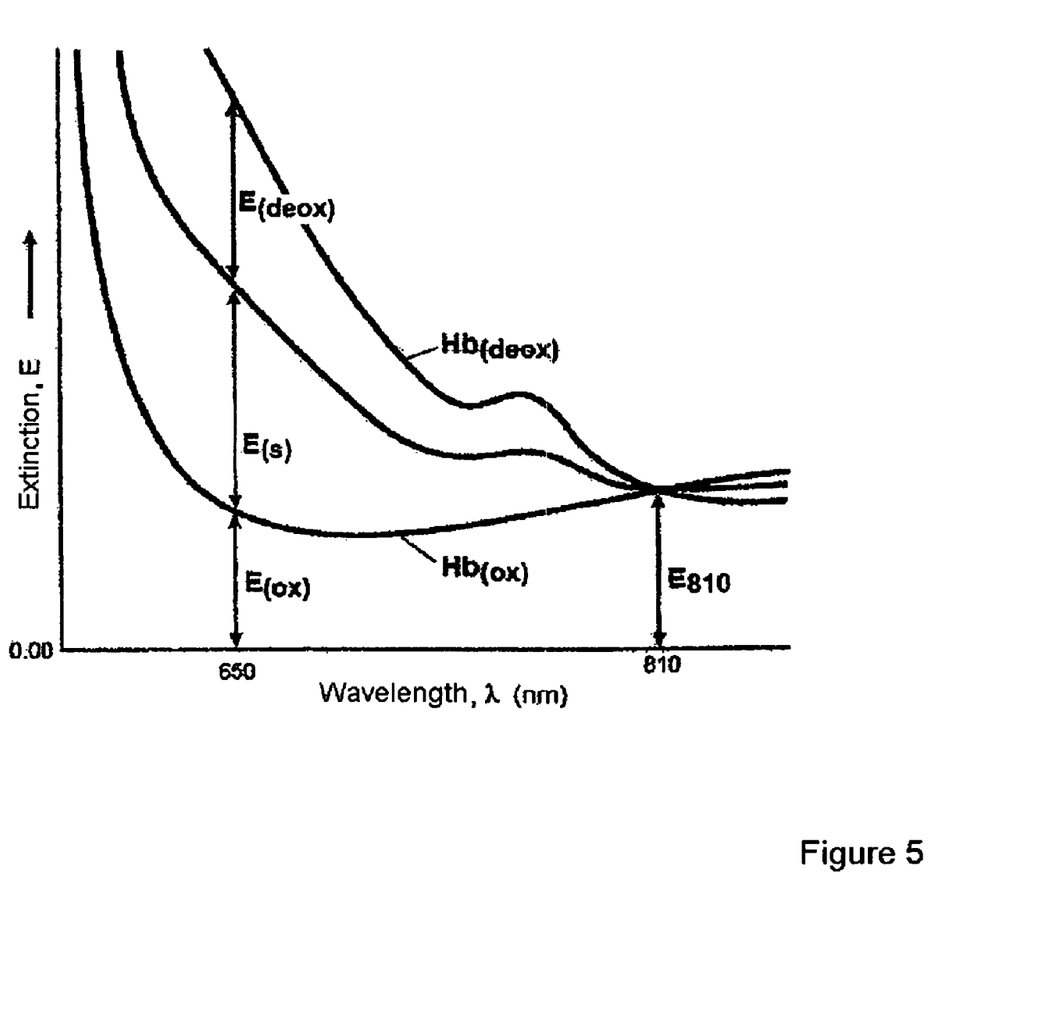
FIG. 5 is a graph showing the wavelength dependency of the absorption strength of the hemoglobin.

To measure the oxygen content of the blood or its oxygen saturation, a spatially resolved determination is made in that recordings are made by the image recording module 4 using at least two different wavelengths. The fact that the absorption spectra of oxygen-rich blood ($HB_{ox}$) and oxygen-starved blood ($HB_{deox}$) differ considerably is made use of for this purpose. FIG. 5 shows a graph of the wavelength dependency of the absorption rate of hemoglobin. Preferred wavelengths are about 650 nm and about 810 nm.

The proposed technical solution provides a device and a method for the observation, documentation and/or diagnosis of the fundus by which the blood flow, or more accurately the blood flow velocity, can be measured at the retina and at the fundus in a spatially resolved manner. Ideally, with slight, reversible modifications, the solution is also suitable for measuring the oxygen content of the blood, and the overall solution can easily be integrated in a conventional fundus camera.

In the method according to the invention for the observation, documentation and/or diagnosis of the fundus, the light of a multi-spectral sequential illumination module is imaged on an image recording module by the eye by means of an ophthalmologic examination device. The illumination module which is connected to the ophthalmologic examination device and comprises at least two individual light sources which can be regulated individually with respect to intensity and duration emit monochromatic light of different wavelengths, preferably in the range from 350 to 900 nm, which is imaged on the image recording module by the ophthalmologic examination device by means of the eye being examined, which image recording module is likewise connected to the ophthalmologic examination device and is tuned to the wavelengths of the light emitted by the multi-spectral illumination module and synchronized with its illumination periods. The control and safety module controls the chronological sequence, duration and intensity of the individual light sources of the illumination module and monitors the light stress on the eye being examined. The evaluating unit regulates the control and safety module and assesses, corrects, improves and combines the recordings of the fundus transmitted by the image recording module for evaluation.

In an advantageous construction, individual light sources whose turn-on and turn-off delay is under 1 ms are used for the illumination module. This means that every beam can be turned on from 0 to 100% intensity within a time period of less than 1 ms and can also be turned off again from 100% to 0 within this time period.

The beam bundles generated by the individual light sources having the narrowest possible band coincide in aperture and aperture angle at the point of connection to the ophthalmologic examination device and preferably generate a circular or annular image with an angular spectrum that is as constant as possible. The optical power of the individual light sources should be at least 1 milliwatt at the interface.

In particular, the control and safety module controls only those individual light sources with appropriate duration and intensity that are required for the specific examination. The control and safety module synchronizes the image recording module with the illumination module so that an image, but preferably also a plurality of associated images, is realized with optimal contrast, i.e., with the highest possible signal-to-noise ratio, at every wavelength. A sensitive monochromatic camera with an average resolution of about 1 megapixel is used as image recording module, for example. The image converter chip of the camera can contain a microlens array to achieve the highest possible surface area fill density.

The chronological order of the individual spectral colors is advantageously selected in such a way that the wavelength causing the least stimulation of the eye, particularly of the pupil reflex, is determined first in time. Therefore, in an advantageous manner, a recording without stimulation should be carried out first in the infrared region, followed by a recording in the red region with slight stimulation. Finally, after a recording is carried out in the blue region with relatively slight stimulation, a recording is made in the green region in which the eye is most sensitive, and maximum stimulation is carried out.

Further, the intensity of the individual spectral colors is advantageously matched to the distribution of the color information of the retina for the recording of color fundus images. The retina has primarily red components (about 60 to 80%) followed by components in the green region (20 to 30%). The proportion of blue color information is the smallest (5 to 15%). Therefore, the multi-spectral illumination should advantageously have a relatively high proportion of red.

As was already described, LEDs, with and without filters arranged in front of them, or diode lasers can be used as individual light sources in particular. The individual light sources are selected in such a way that sensitive and highly resolved images of the retina are recorded and information about possible diseases can be diagnosed by electronic post-processing and evaluation.

The evaluating unit processes the images supplied by the image recording module with respect to contrast, image sharpness, color errors, pixel errors, border falloff, distortion, local alignment error, and the like. But at least one image, preferably a plurality of images, is recorded in different colored illumination states with an exposure time of several milliseconds.

In particular, the individual images supplied by the image recording module are evaluated by the evaluating unit with respect to their quality, existing image errors such as image sharpness, pixel errors, border falloff, and distortion are corrected, the quality of the recordings is improved with respect to contrast and sharpness, and relevant information for functional diagnostics is extracted.

For example, differences in contrast can be compensated in that, instead of a monochrome recording with white-light illumination of the fundus, the image recording module 4 carries out three monochromatic recordings with illumination by blue, green and red light, and the evaluating unit 7 calculates a total recording from these three recordings.

In one embodiment of the method, the fundus is illuminated by the multi-spectral sequential illumination module 1 and at least two immediately successive recordings are carried out by the image recording module 4 at different exposure times and are sent to the evaluating unit 7 for spatially resolved combination and evaluation. In particular, a first recording of the fundus is made by the image recording module 4 with a normal exposure time and an immediately succeeding second recording is made with overexposure, the overradiated areas are cut out from the overexposed image by the evaluating unit 7 and replaced by the corresponding areas of the normally exposed recording to obtain a dynamic recording.

In another advantageous embodiment for measuring the blood flow at the fundus, at least one individual light source of the multi-spectral sequential illumination module 1 emits spatially and temporally highly coherent light, and a laser which is preferably operated in pulsed mode is used as this individual light source.

For this purpose, the fundus is illuminated with spatially and temporally very coherent light by the multi-spectral sequential illumination module 1 for measuring the blood flow, recorded by the image recording module 4 in the form of at least two recordings with high temporal resolution, and sent to the evaluating unit 7 for a spatially resolved correlation analysis for determining the distance and direction of the blood flow. To determine the blood flow velocity, at least two other recordings are made with high temporal resolution with spatially and temporally very coherent illumination of the fundus and sent to the evaluating unit 7 for a spatially resolved correlation analysis. The image recording module 4 is controlled by the control and safety module 5 synchronous to the illumination module 1 operating in pulsed mode.

In a particularly advantageous embodiment, a commercially available digital camera is used for the image recording module 4. In a commercially available digital camera with a resolution of 1 megapixel, for example, the readout and storage of the image displayed on the chip takes about 60 ms. However, this temporal resolution is not sufficient for registering the fast speckle movements. In order to achieve the high time resolution, the following illumination method and image recording method are used.

For the double recordings of high temporal resolution with spatially and temporally very coherent illumination, the pulsed illumination module 1 is controlled by the control and safety module 5 in such a way that a first illumination flash is triggered at the end of the exposure period for the first recording and a second illumination flash is triggered at the start of the exposure period for the second recording. Accordingly, the temporal resolution for this double image is essentially limited only by the flash time of the laser and thus, in practice, can be reduced to a few microseconds.

In a first method step, the two images of the fundus taken by the image recording module 4 with high temporal resolution for a spatially resolved correlation analysis for determining the distance and direction of the blood flow are sent to the evaluating unit 7. The correlation of the two images with one another shows the displacement of the fundus during the measurement in distance and direction. When the images are subtracted from one another, a (speckled) uniformly gray area with highlighted brighter vessels is seen. The reason for the bright vessels has to do with the blood flow within the vessels.

However, in order to derive information about the blood velocity from the difference in brightness between the vessels and the fundus, it must be determined how much light is backscattered from the wall of the vessels and how much light is backscattered from the blood flow within the vessels. For this purpose, at least two additional recordings of high temporal resolution are made with spatially and temporally very coherent illumination of the fundus and sent to the evaluating unit 7 for a spatially resolved correlation analysis.

These two double images are correlated with one another, then subtracted from one another and the results of the subtraction are then used to measure the difference in brightness of the vessels with respect to the fundus. It can then be determined from this value, as a function of the two time intervals of the double images, how much light from the blood flow is backscattered and at what absolute velocity the blood flows in the vessels. In order to achieve the time resolution with as few images as possible, it is also possible, as was described, to record double images within a very brief time sequence and to vary the pulse duration of the two individual pulses at the same time. In this case, the blood flow velocity can also be determined from the characteristics of the autocorrelation function of portions of the fundus images.

The images of the fundus camera show the fundus of the eye being examined through a circular mask. Images or film sequences of a plurality of images of the fundus are recorded and evaluated. Since all of the images of the sequence are compared with the first image, it must be ensured that the first image is as sharp as possible and contains no motion blur or interlace artifacts. A square partial image with $2^n \times 2^n$ pixels (n=6 . . . 8) is selected from the central image region in every image. The partial image is selected for each film in such a way that the partial image contains as many sharp structures as possible because this improves the accuracy of the correlation. The partial images are designated by TB1 . . . TBn. The cross-correlation functions of the images of the sequence relative to the first image of the sequence are designated by K(TBn; TB1). The cross-correlation function is then given by:

$$F[K(TBn;TB1)] = F[TBn] \cdot F[TB1]^*$$

$$K(TBn;TB1) = F^{-1} |F[TBn] \cdot F[TB1]|,$$

where F is the operator for the Fourier transform;
$F^{-1}$ is the operator for the inverse transform; and
* is the complex conjugate.

The size of the partial images must be optimized in order to optimize the speed and accuracy of the method. The speed for the calculation of the fast two-dimensional FFT of an image of m×m pixels is proportional to:

$$m^2 \cdot \ln(m)$$

The two-dimensional FFT, in which the FFT is calculated first by every row and then by every column, yields a two-dimensional image in Fourier space. The quantity m of the partial images must be selected in such a way that, first, it is appreciably greater than the maximum expected displacement of the images and, second, does not fall below a minimum quantity so that the errors in the correlation function which are caused by the pixel noise of the camera images average out over the partial images. For typical images of the fundus, it has proven useful when m=64, 128 and 256 pixels.

The pixel with the maximum brightness is the next to be determined in the cross-correlation function. If the pixel with coordinates (0, 0) is the brightest, the two images are not displaced relative to one another. If another pixel in the correlation function is the brightest, the distance and the direction to the coordinate origin indicate the strength and direction of the displacement (correlation images are continued in the origin periodically in the x and y directions). The accuracy with which the displacement is determined is a maximum of one pixel. The images corrected by the determined value of the displacement can be superimposed and color images or averaged monochromatic images can be determined by the evaluating unit.

The basic principle of image averaging consists in that the images are correlated with one another to determine the image displacement between recordings. Using this data, a plurality of images can be superimposed in a pixel-correct manner and averaged. This yields images with less pixel noise, i.e., with improved image contrast.

In particular, the determined value of the displacement can be used to superimpose a plurality of individual images recorded in one color without errors and to average them to obtain images with a higher contrast, i.e., less noise, that is, images which are more dynamic.

However, it is also possible to use the determined value of the displacement to superimpose individual images recorded in different colors (color partial images) without errors and to determine a color image of the fundus in this way. This has the advantage that color LEDs with very high spectral intensity can be used. With this type of measurement, the color information of the fundus image is obtained through the color illumination instead of through a color mask in front of the receiver chip.

In live fundus observation, for example, all of the partial images can be measured, stored and then superimposed in the video clock. This would obviate the need for a pulsed recording with a flash light source and would nevertheless yield images with comparable or higher dynamics.

It has been shown that this method generates images having a brightness at least ten times greater than when using a white-light source with an RGB camera.

In another modification of the method step, the color partial images would be averaged over different numbers of images. The reason for this resides in the spectral characteristics of the fundus. A color image of the fundus carries the majority of information in the red portion of the image (because the fundus is reddish). Therefore, it would be necessary to average many more partial images in the red color region than for the other color partial images. The image would appear less noisy after superposition and thus the best signal-to-noise ratio would be achieved in the shortest measuring time.

The most important advantage of the method consists in the possibility of substantially increasing the resolution of the images.

For this purpose, a method is used which can be considered as prior art but which has been substantially modified in one respect. This method will now be briefly described.

First, $n^2$ images are recorded which are displaced by the nth of a pixel relative to one another in the x direction and, independently, in the y direction. The $n^2$ images supplied by the image recording module and recorded with a displacement in each instance by the nth of a pixel in the x direction and the y direction are written by the evaluating unit pixel by pixel into an image field whose size is n-times as large such that n columns and n rows remain free for the other images, i.e., the $n^2$ images are nested. The whole image field which is n-times as large in each direction is then subjected to Fourier transformation and divided by the Fourier transformation of the distribution of a correction image. This image is then transformed back by an inverse Fourier transform, and an image with n-times resolution is accordingly determined. The correction in Fourier space is necessary because the nested images were recorded with pixels which were too large relatively. For this purpose, as was described, the images with increased resolution (preferably in Fourier space) are deconvoluted with a correction image. The correction image has the same number of pixels as the image with increased resolution and all of the pixels have the value of zero with the exception of a square image region with n·n pixels with the values $1/n^2$. This correction image is transformed to Fourier space and the quantity of this complex function is determined. The image with increased resolution is likewise transformed to Fourier space and divided by the amount of the Fourier transform (FFT) of the correction function. The image thus calculated is transformed back to real space and is now almost entirely equivalent mathematically to an image with n-times resolution.

To double the resolution, for example, an image with a resolution of 1000×1000 pixels is recorded. Then, the image is shifted first horizontally by a half-pixel, then vertically by a half-pixel, then back horizontally by a half-pixel, then back vertically by a half-pixel on the image recording module for another recording. The four images obtained in this way are nested to yield an image having twice the resolution in both directions. Of course, the pixels with which the total image with twice the resolution was recorded are twice as large as they need to be so that even though the image has twice the resolution the sharpness of the image is worse than that of an image of a camera with 4 megapixels. This problem can be overcome when the nested image is corrected in Fourier space by subjecting the image to a Fourier transformation and dividing it by the complex amount of the Fourier transformation of the distribution of a correction image. The correction image is an image with 1000×1000 pixels with the value of zero and 2×2 pixels with the value of ¼. The inverse transform of the image corrected in this way yields an image with genuinely twice the resolution in every spatial direction.

To triple the resolution, nine images are recorded with a displacement of one third of a pixel in each instance. For the most part, higher increases in resolution are not useful because the noise contained in the image is also amplified by the Fourier correction.

The essential difference over the prior art can be described as that the images are not actively displaced with respect to one another, but rather the saccadic movement of the eye is made use of for the image displacement in the subpixel range. This means recording statistical image displacements through the saccadic movement. Accordingly, the image displacements need no longer be adjusted with subpixel accuracy, but rather need only be calculated by a correlation with subpixel accuracy.

The correlation resolution can be increased considerably when the peak in the correlation image, which is at most several pixels wide in any direction, is approximated by a function such as, for example, a parabola with variable width and vertex position. Thus, the position of the maximum of the correlation function and, therefore, also of the relative image displacement in relation to the first image can be determined with subpixel accuracy and it is precisely this which makes it possible to apply the algorithms for increasing resolution which were just described.

In particular, the displacement of the images supplied by the image recording module is determined in the subpixel range by the evaluating unit in that the brightest pixel of the correlation image and its two closest neighbors in x direction are determined and the following system of equations is solved:

$$y_1 = A \cdot (x_1 - x0)^2 + B$$

$$y_2 = A \cdot (x_2 - x0)^2 + B$$

$$y_3 = A \cdot (x_3 - x0)^2 + B,$$

the value of the determined displacement is split into the integral part and the subpixel remainder, the images are displaced in such a way that the entire amount of the determined displacement is compensated, and this procedure is repeated once more for the y direction.

To double the resolution, the images which are supplied by the image recording module and are displaced by the integral portion in the x direction and y direction are written by the evaluating unit into an image field which is twice as large with respect to pixels in such a way that the values with an even-numbered pixel index form partial image 1 and the values with an odd-numbered pixel index form partial image 2, and a counter variable that is set to zero is assigned to each partial image. In so doing, an image whose subpixel remainder of the displacement with respect to the reference image is between 0.25 and 0.75 is added to partial image 1 and the corresponding counter variable is increased by 1, an image whose subpixel remainder of the displacement with respect to the reference image is between 0 and 0.25 or between 0.75 and 1 is added to partial image 2, and the corresponding counter variable is increased by 1, this procedure is repeated for all of the images and in an equivalent manner for the y direction, and an image with twice the resolution is formed by dividing the partial images by the associated counter variables.

For this purpose, in particular, the displacements of the images relative to one another must be determined with subpixel accuracy. For this purpose, a master partial image is selected first and all of the individual images must be cross-correlated with it.

In the next step, two parabolas are adapted to the brightest pixel and its closest two neighbors in the x direction and y direction of the correlation function by solving the system of equations above with three equations and three unknown parameters for the two parabolas. The position of the intensity maximum yields the displacement of the images relative to the master image. To calculate the increased-resolution image, a new image with twice the resolution in two spatial directions is, applied, and 2×2 pixels are now assigned to a pixel of the original image. The images of the sequence are shifted back by the entire amount of the pixel displacement. Accordingly, the images are now displaced in every case by less than one pixel relative to the master image. Next, the partial images are added to the image with twice the resolution. The size of the subpixel displacement determines which one of the four sub-images the partial images are added to. The subpixel displacement is divided into intervals and every interval is associated with a sub-image. The sub-images which are summed in this way are divided by the respective quantity of images so as to obtain a mathematical average.

These process steps result in an image with twice the resolution. However, this image differs from an image recorded by a camera chip with twice the resolution. Since the camera pixels do have a size that corresponds to the ordinary resolution, it is indeed possible to acquire more data points by repeated sampling with subpixel displacements. However, owing to the pixels of the camera which are too large relatively, high spatial frequencies are suppressed or attenuated in the image with increased resolution. But this effect can be compensated in Fourier space by a corresponding inverse filter. The high spatial frequencies in the image are amplified by this filter. Therefore, the image appears sharper but also noisier.

The algorithm is slightly modified for tripling the resolution. In this case, three partial images with subpixel displacements in the intervals ($\frac{1}{6} \ldots \frac{3}{6}, \frac{3}{6} \ldots \frac{5}{6}, \frac{5}{6} \ldots \frac{1}{6}$) are applied in every direction, and the images are sorted into these interval categories according to the size of the subpixel displacement.

In the method steps described so far, it is especially important that the images selected for further processing contain no defects or as few defects as possible.

The size m of the partial images must be selected in such a way that, first, they are appreciably larger than the maximum expected displacement of the images and, second, that they do not fall below a minimum size so that the errors caused in the correlation function by the pixel noise of the camera images are averaged out over the partial images. A poor choice of partial images can result in additional errors.

Figure 2:
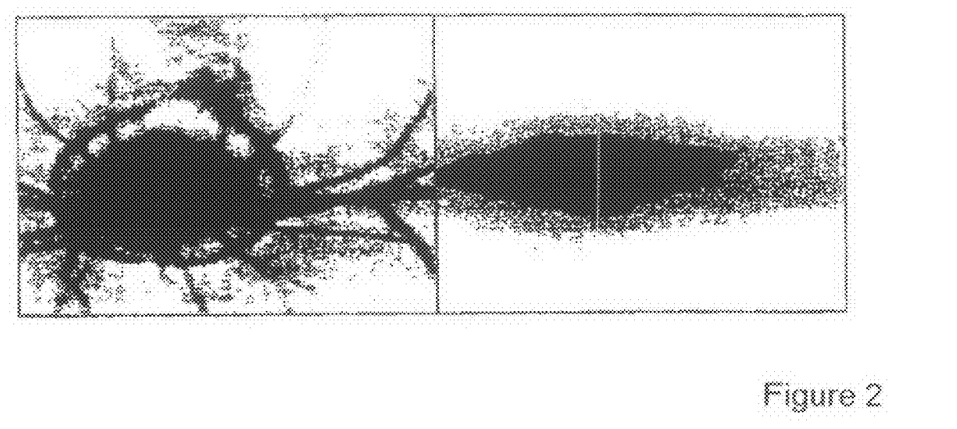
FIG. 2 illustrates a poorly chosen partial image and the outcome of the resulting correlation function.
Figure 3:
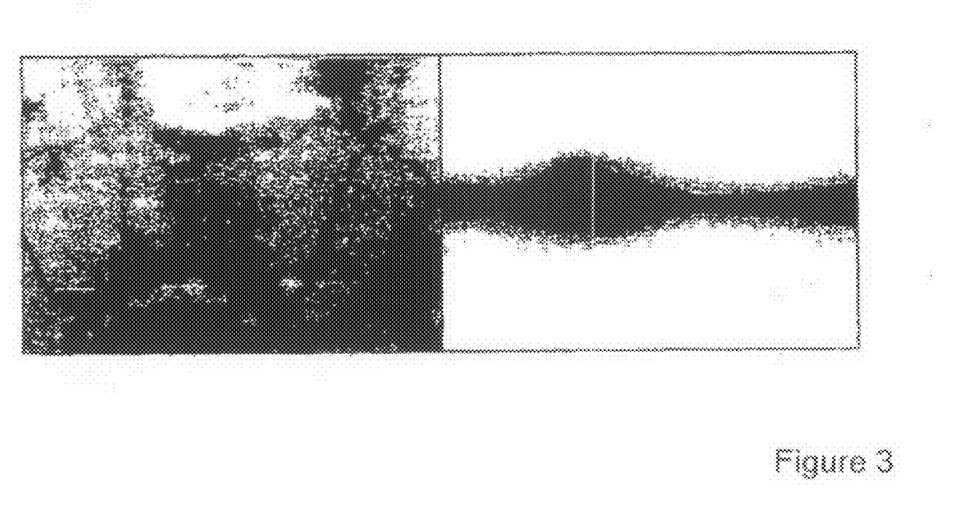
FIG. 3 illustrates a suitable partial image and the outcome of the resulting correlation function.

For example, if there are sharp variations in brightness at the borders of the partial images selected for the calculation of the correlation function, artifacts can be caused in the cross-correlation function. FIG. 2 shows a poorly selected partial image and the outcome of the resulting correlation function. The brightest pixel cannot be determined in this case. However, these artifacts can be prevented by choosing a suitable partial image. FIG. 3 shows a suitable partial image with the outcome of the resulting correlation function. For this reason, it must be ensured for all further evaluations that the best possible partial images are cut out for the partial images.

For this purpose, in particular, a region should be selected from the fundus image in which there are image elements such as vessels, deposits, or the like which are clearly structured in x direction and y direction. Further, it must be ensured either that the partial images are illuminated relatively uniformly or that the brightness at the border of the image region does not vary widely. For this reason, a partial image around the bright papilla of the eye was selected in the angiographic recordings in which the vessels are to be detected as bright structures.

The displacement with subpixel accuracy, which is important for de-blurring, is determined from the correlation function between the master image and a sequential image. The narrower and brighter the correlation peak, the greater the accuracy. Therefore, the selected image must have as little interlacing and blurriness as possible. Also, for calculating the averaged and/or increased-resolution image, it is very important to eliminate blurry or interlaced images because they impair (blur) the final image of the algorithms.

Therefore, the goal is to use an algorithm for sorting out blurry or interlaced images which detects the unsuitable image in the most automated and fastest way possible. For this reason, in order to derive measurements for the level of image sharpness and interlace errors, it was attempted to rely on image quantities that are already calculated.

The images supplied by the image recording module are examined for interlace defects by the evaluating unit by generating two-dimensional Fourier transforms, determining the location of the highest spatial frequencies (sum of the pixel values of the mean row and mean column of the two-dimensional Fourier image), and dividing the two values. Images in which the quotient of these two values deviates appreciably from 1 contain interlace defects and are not further processed.

In a so-called interlaced camera, two fields are read out with, respectively, all even lines and, in the next cycle, all odd lines. The time between the readout processes of the two fields is about 20 ms. In this time, the image of the fundus on the camera can shift, as a result of which the two camera fields can be displaced relative to one another. This displacement of the two fields leads to image errors when the images are averaged and when resolution is increased.

Since the two fields can be displaced relative to one another in two directions, it is not possible in principle to compensate for the interlace error computationally. To prevent images having these artifacts from being processed by the algorithms for increasing resolution and thereby blurring the final image, these images must be eliminated definitively.

This can be carried out, for example, in that an image region is cut out and transformed to frequency space with the algorithms of the FFT for calculating the correlation. The interlace errors are caused by movements during the sequential recording of the fields with even and odd line indexes. These errors lead to the typical "frayed" vertical edges in the image. This increases the frequency components with the highest spatial frequency in the frequency spectrum of the image columns.

However, this increase cannot detected in the frequency spectrum of the rows. Therefore, the following two-dimensional FFT is calculated from the image ($x_i$, $y_j$):

$$FFT_{image}(vx_i, vy_j),$$

where i, j designate 0 . . . 256, x is the row coordinate, and y is the column coordinate.

The following two quantities are derived from this image:

$$S_{vx} = \sum_{\forall i} FFT_{image}(vx_i, vy_{127})$$

$$S_{vy} = \sum_{\forall j} FFT_{image}(vx_{127}, vy_j).$$

If the image is similarly structured in the x direction and y direction and no interlace artifacts occur, the quotient $S_{vy}/S_{vx}$ should be close to 1. If interlace artifacts occur, the quotient increases. The following threshold has proven useful for sorting out the interlaced images:

$$\frac{S_{vy} - S_{vx}/2}{S_{vx}/2} \quad \begin{array}{l} <4 \text{ images are not interlaced} \\ >4 \text{ images are interlaced} \end{array}$$

This calculation is recommended for the master image and each individual image of the sequence if the images are to be processed in a fully automated manner.

Sorting out blurry images is considerably more difficult because no absolute threshold can be defined as it can with interlace defects. A relative valuation of the sharpness of the individual images of the sequence can be realized in the following manner. The correlation function is calculated from the master image and the individual image. The brightest pixel of this function and its closest two neighbors in x direction are approximated by a parabola with the equation $$y = A \cdot (x-x0)^2 + B$$

and by the three parameters A, x0 and B to be determined. The quantity x0 is the sought-for displacement of the two images with subpixel accuracy. Quantity A is a measure of the width of the cross-correlation function between the master image and individual image and therefore, given a fixed master image, is a relative measure for the sharpness of the individual image. This computation is repeated for the y direction. If one of the two parameters $A_x$, $A_y$ exceeds a determined suitable threshold, the image is sorted out as blurry. The calculation of quantities $A_x$, $A_y$ requires no substantial additional computing time since it occurs as an extra result in determining x0.

To select the sharpest image from a sequence as the master image, the described algorithm for the autocorrelation function of the individual images can be carried out. The sharpest image is the image with the smallest A parameters. In contrast to the determination of the sharpness of the individual images in the correlation against the master image, however, this computation is considerably more elaborate.

The device and the method according to the invention for observation, documentation and/or diagnosis of the fundus provide a solution which makes possible a sequential multi-spectral illumination of the retina with high viewing angles and which minimizes the light stress on the eye being examined in that excitation is carried out only with the wavelengths which are also used for evaluation.

The multi-spectral sequential illumination module based on monochromatic LEDs makes it possible to illuminate the object under examination with an illumination which can be adjusted to a narrow spectrum and can be switched quickly. By superimposing sequential images of a monochromatic, sensitive, high-resolution camera, it is possible, by means of subsequent electronic processing, to carry out fluorescence recordings, monochromatic recordings and color recordings as well as a diagnostic evaluation with the least possible radiation stress on the retina.

It is advantageous to use only one individual monochromatic digital camera. With the exception of fluorescence recordings in which a filter is inserted into the observation beam path, all mechanically moving parts such as filters and shutters can be done away with.

The method according to the invention provides a solution which makes it possible to determine the blood flow velocity in the vessels of the fundus. The blood flow velocity value, in connection with information about $O_2$ saturation in the fundus, also provides information about the amount of oxygen stored in the tissue. In this way, disturbances in circulation and particularly in the metabolism can be diagnosed.

While the foregoing description and drawings represent the present invention, it will be obvious to those skilled in the art that various changes may be made therein without departing from the true spirit and scope of the present invention.

What is claimed is:

1. A device for the observation, documentation and/or diagnosis of the fundus, comprising:
    an ophthalmologic examination device;
    a multi-spectral sequential illumination module;
    an image recording module;
    a control and safety module; and
    an evaluating unit;
    wherein the illumination module is connected to the ophthalmologic examination device, and has at least two individual light sources which can be regulated individually with respect to intensity and duration and which emit monochromatic light of different wavelengths;
    wherein light coming from the illumination module is imaged on the image recording module from the ophthalmologic examination device by the eye being examined;
    wherein said image recording module, which is likewise connected to the ophthalmologic examination device, is tuned to the wavelengths of the light emitted from the illumination module and synchronized with its illumination periods of the light emitted from the illumination module; and
    wherein said control and safety module controls the chronological sequence, duration, and intensity of the individual light sources of the illumination module, and monitors the light stress; and
    wherein said evaluating unit regulates the control and safety module and assesses, corrects, improves, combines, superimposes in a positionally exact manner, and evaluates the recordings of the fundus transmitted by the image recording module.

2. The device according to claim 1,
    wherein the illumination module preferably emits monochromatic radiation in the transparent range of ocular media from 350 nm to 900 nm and from 1000 nm to 1150 nm, wherein the individual light sources have a spectral half-intensity width of less than 40 nm.

3. The device according claim 1;
    wherein at least one individual light source of the multi-spectral sequential illumination module emits light which is very coherent spatially and temporally.

4. The device according to claim 1;
    wherein the individual light source of the illumination module emitting spatially and temporally very coherent light is a laser which is preferably operated in pulsed mode.

5. The device according to claim 1;
wherein a variable scatter filter or a rotating mirror is provided for reducing the coherence of laser radiation for two-dimensional illumination of the fundus at very high radiation intensities.

6. The device according to claim 1;
wherein the illumination module has at least one individual light source in the form of a pulsed gas discharge light source for two-dimensional, high-energy illumination of the fundus.

7. The device according to claim 1;
wherein individual light sources whose turn-on delay and turn-off delay are under 1 ms are used for the illumination module.

8. The device according to claim 1;
wherein the individual light sources are arranged in two dimensions or three dimensions.

9. The device according to claim 1;
wherein the beam bundles generated by the individual light sources coincide in aperture and aperture angle at the point of connection to the ophthalmologic examination device and generate an image with the most constant possible angular spectrum at that point.

10. The device according to claim 1;
wherein mirrors, dichroic mirrors, and/or gratings are used to couple the beam bundles generated by the individual light sources.

11. The device according to claim 1;
wherein a light guide or light-guide bundle, a light-mixing rod, or a microlens array is arranged between the illumination module and the ophthalmological examination device for transmitting the light of the individual light sources.

12. The device according to claim 1;
wherein the control and safety module drives only those individual light sources with the corresponding duration and intensity that are required for the specific image.

13. The device according to claim 1;
wherein the control and safety module drives the individual light sources in order of the level of stimulation of the eye brought about by them, starting with the individual light source producing the least stimulation.

14. The device according to claim 1;
wherein the control and safety module adapts the duration and intensity of the individual light sources to the distribution of the color information of the object to be illuminated.

15. The device according to claim 1;
wherein the control and safety module synchronizes the image recording module with the illumination module so that an image, or preferably also a plurality of associated images, is realized with optimal contrast at every wavelength.

16. The device according to claim 1;
wherein the image recording module comprises a sensitive monochromatic camera with a microlens array arranged in front of its image converter chip.

17. The device according to claim 1;
wherein the images supplied by the image recording module are further processed by the evaluating unit with respect to contrast, image sharpness, color errors, pixel errors, border falloff, distortion, local alignment error, and the like.

18. The device according to claim 1;
wherein an averaged image or a color image of the fundus is determined by the evaluating unit from a plurality of monochromatic images supplied by the image recording module.

19. The device according to claim 1;
wherein an image with a resolution that is increased n-times in every spatial direction is calculated by the evaluating unit from a plurality of individual images supplied by the image recording module.

20. The device according to claim 1;
wherein the ophthalmologic examination device is a fundus camera operating on the mydriatic principle or on the non-mydriatic principle.

21. The device according to claim 1;
wherein for the purpose of measuring blood flow a first polarization filter is arranged in front of the multi-spectral sequential illumination module for illuminating the fundus with polarized light, and a second polarization filter is arranged in front of the image recording module for detecting the light that is scattered multiple times and depolarized.

22. The device according to claim 1;
wherein the polarization filters which are arranged in front of the multi-spectral sequential illumination module and in front of the image recording module, respectively, are constructed as linear or circular polarizers.

23. The device according to claim 1;
wherein at least one birefringence compensator is provided to compensate for the birefringence of the cornea, eye lens, retina and/or optical components of the ophthalmologic examination device.

24. The device according to claim 1;
wherein a variable birefringence compensator with a position-dependent compensation characteristic is preferably used as birefringence compensator.

25. The device according to claim 1;
wherein for measuring the oxygen content of the blood the fundus is illuminated by the multi-spectral sequential illumination module with two different wavelengths and recorded by the image recording module and the recordings are sent to the evaluating unit.

26. The device according to claim 1; wherein for measuring the oxygen content of blood, at least one color filter is arranged in front of the multi-spectral sequential illumination module or in front of the image recording module, and recordings of the fundus are made by the image recording module with and without a color filter and are sent to the evaluating unit.

27. The device according to claim 1;
wherein for measuring the oxygen content of blood, two color filters are arranged in front of the multi-spectral sequential illumination module or in front of the image recording module and are successively introduced into the beam path so that recordings of the fundus are made by the image recording module with both color filters and are sent to the evaluating unit.

28. The device according to claim 1;
wherein the measurement of the oxygen content of the blood is carried out with the color filters preferably at wavelengths of about 650 nm and 810 nm.

29. The device according to claim 1;
wherein polarization filters, birefringence compensators and color filters are constructed in such a way that they can be swiveled out of the beam path.

30. The device according to claim 1;
wherein the ophthalmologic examination device has an arrangement for detecting and compensating for eye movement.

31. The device according to claim 1;
wherein the acquired data in the form of individual recordings, combined individual recordings and individual recordings processed by software, and recordings of live sequences with at least 10 frames per second are stored in an updated and permanent manner by the evaluating unit.

32. A method for the observation, documentation and/or diagnosis of the fundus, comprising the steps of:
imaging the light of a multi-spectral sequential illumination module on an image recording module by the eye by an ophthalmologic examination device;
connecting the illumination module to the ophthalmologic examination device, said illumination module comprising at least two individual light sources which can be regulated individually with respect to intensity and duration emit monochromatic light of different wavelengths which is imaged on the image recording module by the ophthalmologic examination device by the eye being examined;
connecting said image recording module to the ophthalmologic examination device, tuning the image recording module to the wavelengths of the light emitted by the illumination module, and synchronizing the image recording module with illumination periods of the illumination module;
providing that a control and safety module controls the chronological sequence, duration, and intensity of the individual light sources of the illumination module, and monitors the light stress on the eye being examined; and
providing that the evaluating unit regulates the control and safety module, and assesses, corrects, improves, combines, superimposes in a positionally exact manner, and evaluates the recordings of the fundus transmitted by the image recording module.

33. The method according to claim 32;
wherein the illumination module preferably emits monochromatic radiation in the transparent range of ocular media from 350 nm to 900 nm and from 1000 nm to 1150 nm, wherein the individual light sources have a spectral half-intensity width of less than 40 nm.

34. The method according to claim 32;
wherein the individual light sources of the illumination module have a turn-on delay and turn-off delay under 1 ms.

35. The method according to claim 32;
wherein the individual light sources generate beam bundles which coincide in aperture and aperture angle at the point of connection to the ophthalmologic examination device and generate a preferably circular or annular image with the most constant possible angular spectrum at that point.

36. The method according to claim 32;
wherein the control and safety module drives only those individual light sources with the corresponding duration and intensity that are required for the respective images of the fundus.

37. The method according to claim 32;
wherein the control and safety module drives the individual light sources in order of the level of stimulation of the eye brought about by them, starting with the individual light source producing the least stimulation.

38. The method according to claim 32;
wherein the control and safety module adapts the duration and intensity of the individual light sources to the distribution of the color information of the object to be illuminated.

39. The method according to claim 32;
wherein the control and safety module synchronizes the image recording module with the multi-spectral illumination module so that an image, or preferably also a plurality of associated images, is realized with optimal contrast at every wavelength.

40. The method according to claim 32;
wherein the image recording module comprises a sensitive monochromatic camera with a microlens array arranged in front of its image converter chip.

41. The method according to claim 32;
wherein the images supplied by the image recording module are further processed by the evaluating unit with respect to contrast, image sharpness, color errors, pixel errors, border falloff, distortion, local alignment error, and the like.

42. The method according to claim 32;
wherein an averaged image or a color image of the fundus is determined by the evaluating unit from a plurality of monochromatic images supplied by the image recording module.

43. The method according to claim 32;
wherein, instead of a monochrome recording with white-light illumination of the fundus, the image recording module carries out three monochromatic recordings with illumination by blue, green and red light, and the evaluating unit calculates a total recording from these three recordings, wherein differences in contrast are compensated and the dynamics are optimally controlled in every partial recording.

44. The method according to claim 32;
wherein the fundus is illuminated by the multi-spectral sequential illumination module, and at least two immediately successive recordings are carried out by the image recording module at different exposure times and sent to the evaluating unit for spatially resolved combination and evaluation.

45. The method according to claim 32;
wherein a first recording of the fundus is made by the image recording module with a normal exposure time and an immediately succeeding recording is made with overexposure, wherein the overradiated areas are cut out from the overexposed image by the evaluating unit and replaced by the corresponding areas of the normally exposed recording to obtain a dynamic recording.

46. The method according to claim 32;
wherein an image with a resolution that is increased n-times in every spatial direction is calculated by the evaluating unit from a plurality of individual images supplied by the image recording module.

47. The method according to claim 32;
wherein the evaluating unit determines the displacement of the images supplied by the image recording module by applying a correlation algorithm from sections of the images.

48. The method according to claim 32;
wherein the evaluating unit superimposes the images corrected by the determined value of the displacement and determines a color image or averaged monochromatic image.

49. The method according to claim 32;
wherein the evaluating unit determines the displacement of the images supplied by the image recording module in the subpixel range by determining the brightest pixel of the cross-correlation of the two images and its two closest neighboring pixels in x direction and solving the system of equations:

$$y_1 = A \cdot (x_1 - x0)^2 + B$$

$$y_2 = A \cdot (x_2 - x0)^2 + B$$

$$y_3 = A \cdot (x_3 - x0)^2 + B,$$

the value of the determined displacement is split into the integral part and the subpixel remainder, the images are displaced in such a way that the entire amount of the determined displacement is compensated, wherein this procedure is repeated once more for the y direction.

50. The method according to claim 49;
wherein the evaluating unit divides a plurality of images into n interval categories of equal width according to the magnitude of their subpixel displacement values in every spatial direction, then takes the mathematical average of all of the images in an interval category, writes the $n^2$ sub-images formed in this way pixel by pixel so as to be nested within one another into an image field whose size is n-times as large in such a way that n columns and n rows remain free for the other images, the image of increased resolution which is n-times as large is then Fourier-transformed and divided by the complex amount of the Fourier transform of the distribution of a correction image, the obtained image is then transformed back by an inverse Fourier transform, and an image with n-times resolution is accordingly determined, wherein the correction image has the same resolution as the image of increased resolution, and all of the pixels of the correction image have the value of zero with the exception of a square with n·n pixels with the values $1/n^2$.

51. The method according to claim 50;
wherein the images which are supplied by the image recording module and recorded so as to be displaced in each instance by the integral portion in the x direction and y direction are written by the evaluating unit into an image field which is twice as large with respect to pixels in such a way that the values with an even-numbered pixel index form partial image 1 and the values with an odd-numbered pixel index form partial image 2, and a counter variable that is set to zero is assigned to each partial image, wherein an image whose subpixel remainder of the displacement with respect to the reference image is between 0.25 and 0.75 is added to partial image 1 and the corresponding counter variable is increased by 1, an image whose subpixel remainder of the displacement with respect to the reference image is between 0 and 0.25 or between 0.75 and 1 is added to partial image 2 and the corresponding counter variable is increased by 1, this procedure is repeated for all of the images and in an equivalent manner for the y direction, and an image with twice the resolution is formed by dividing the partial images by the associated counter variables.

52. The method according to claim 32;
wherein the evaluating unit examines the images supplied by the image recording module for interlace errors in that the averaged rows and averaged columns are Fourier-transformed, the location of the highest spatial frequency in both functions is determined, and the two values are divided, images whose quotient deviates appreciably from 1 contain interlace errors and are not further processed.

53. The method according to claim 32;
wherein the evaluating unit detects blurry images supplied by the image recording module in that the brightest pixel of an image and its closest two neighbors in x direction are determined and approximated by a parabola with the equation $$y = A \cdot (x - x0)^2 + B$$

and is eliminated when quantity A exceeds a limiting value, wherein this procedure is repeated once again for the y direction.

54. The method according to claim 32;
wherein the fundus is illuminated by polarized light by the multi-spectral sequential illumination module for measuring blood flow, and only the light that is reflected by the fundus, scattered repeatedly, and depolarized is recorded by the image recording module in the form of at least two immediately successive recordings and sent to the evaluating unit for a spatially resolved correlation analysis.

55. The method according to claim 32;
wherein the fundus is illuminated by linearly or circularly polarized light.

56. The method according to claim 32;
wherein the birefringence of the cornea, eye lens, retina and/or optical components of the ophthalmologic examination device is compensated by at least one birefringence compensator.

57. The method according to claim 32;
wherein the birefringence is preferably compensated by a variable birefringence compensator with a position-dependent compensation characteristic.

58. The method according to claim 32;
wherein for measuring the oxygen content of the blood, recordings are made of the fundus by the image recording module in two different wavelengths and are sent to the evaluating unit.

59. The method according to claim 32;
wherein the fundus is recorded in two different wavelengths by using at least one color filter which is arranged in front of the illumination module or in front of the image recording module and inserted into the beam path for a recording.

60. The method according to claim 32;
wherein the fundus is recorded in two different wavelengths by using two color filters which are arranged in front of the illumination module or in front of the image recording module and inserted into the beam path for each recording.

61. The method according to claim 32;
wherein the color filter or color filters is or are constructed in such a way that recordings of the fundus can preferably be realized at approximately 650 nm and approximately 810 nm.

62. The method according to claim 32;
wherein the fundus is illuminated with spatially and temporally very coherent light by the multi-spectral sequential illumination module for measuring the blood flow, recorded by the image recording module in the form of at least two recordings with high temporal resolution, and sent to the evaluating unit for a spatially resolved correlation analysis for determining the distance and direction of the blood flow, wherein to determine the blood flow velocity at least two other recordings are made with high temporal resolution with spatially and temporally very coherent illumination of the fundus and sent to the evaluating unit for a spatially resolved correlation analysis, wherein the recordings can be made in different exposure times and the characteristics of the autocorrelation function of partial images are used to determine the blood flow velocity.

63. The method according to claim 32;
wherein the image recording module is controlled by the control and safety module synchronous to the illumination module which preferably operates in pulsed mode.

64. The method according to claim 32;
wherein, for the double recordings of high temporal resolution with spatially and temporally very coherent illumination, the pulsed illumination module is controlled by the control and safety module in such a way that a first illumination flash is triggered at the end of a first exposure period and a second illumination flash is triggered at the start of the second exposure period, and a commercially available digital camera can accordingly be used as image recording module.

65. The method according to claim 32;
wherein eye movement is detected and compensated by the tracking of the sensor of the image recording module.

66. The method according to claim 32;
wherein the acquired data in the form of individual recordings, combined individual recordings and individual recordings processed by software, and recordings of live sequences with at least 10 frames per second are stored in an updated and permanent manner by the evaluating unit.

* * * * *